United States Patent
Augier et al.

(10) Patent No.: US 11,207,657 B2
(45) Date of Patent: Dec. 28, 2021

(54) OLIGOMERIZATION METHOD USING A REACTION DEVICE COMPRISING A DISPERSION MEANS

(71) Applicant: IFP Energies nouvelles, Rueil-Malmaison (FR)

(72) Inventors: Frederic Augier, Saint Symphorien D'Ozon (FR); Alexandre Vonner, Mions (FR); Ludovic Raynal, Oullins (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/629,865

(22) PCT Filed: Jul. 6, 2018

(86) PCT No.: PCT/EP2018/068375
§ 371 (c)(1),
(2) Date: Jan. 9, 2020

(87) PCT Pub. No.: WO2019/011806
PCT Pub. Date: Jan. 17, 2019

(65) Prior Publication Data
US 2021/0077977 A1  Mar. 18, 2021

(30) Foreign Application Priority Data
Jul. 10, 2017 (FR) .................... 17/56.517

(51) Int. Cl.
*B01J 19/18* (2006.01)
*B01J 4/00* (2006.01)
*C07C 2/08* (2006.01)

(52) U.S. Cl.
CPC .......... *B01J 19/1881* (2013.01); *B01J 4/001* (2013.01); *C07C 2/08* (2013.01); *B01J 2219/00103* (2013.01)

(58) Field of Classification Search
CPC .......... B01J 19/1881; B01J 2219/00103; B01J 4/001; B01J 4/002; B01J 4/004; C07C 2/08
See application file for complete search history.

(56) References Cited

U.S. PATENT DOCUMENTS 2,436,767 A * 2/1948 Gerlicher .................. B01J 19/18
526/88
9,475,738 B2  10/2016 Weber et al.
(Continued)

FOREIGN PATENT DOCUMENTS

CA  2767615  8/2013
CN  105693448 A  6/2016
(Continued)

OTHER PUBLICATIONS

International Search report PCT/EP2018/068375 dated Oct. 24, 2018 (pp. 1-3).

*Primary Examiner* — Lessanework Seifu
(74) *Attorney, Agent, or Firm* — Millen, White, Zelano and Branigan, P.C.; Harry B. Shubin (57) ABSTRACT

The present invention relates to an oligomerization process using a reaction device comprising a dispersion means. In particular, the process relates to the oligomerization of ethylene to give linear α-olefins, such as 1-butene, 1-hexene or 1-octene, or a mixture of linear alpha-olefins.

18 Claims, 3 Drawing Sheets

(56) References Cited

U.S. PATENT DOCUMENTS

2011/0257350 A1 10/2011 Jaber et al.
2017/0081257 A1 3/2017 Kreischer

FOREIGN PATENT DOCUMENTS

| EP | 1939163 A1 | 7/2008 |
|---|---|---|
| JP | 2013095671 A | 5/2013 |
| WO | 13095720 A1 | 6/2013 |
| WO | 13116922 A1 | 8/2013 |

\* cited by examiner

FIG 1

PRIOR ART

OLIGOMERIZATION METHOD USING A REACTION DEVICE COMPRISING A DISPERSION MEANS

TECHNICAL FIELD

The present invention relates to an oligomerization process using a reaction device; in particular, the process relates to the oligomerization of ethylene to give linear alpha-olefins, such as 1-butene, 1-hexene or 1-octene, or a mixture of linear alpha-olefins.

PRIOR ART

The invention relates to the field of oligomerization processes using gas/liquid reactors also referred to as bubble-point reactors because they operate under conditions that allow the coexistence of two liquid and gas phases. Due to the exothermic nature of the oligomerization reactions, bubble point reactors also comprise a recirculation loop that consists in withdrawing a liquid fraction, cooling it and reintroducing it into the reaction chamber. Said recirculation loop makes it possible to obtain good homogeneity of the concentrations and to control the temperature throughout the reaction volume, owing to the good heat transfer capacity related to the recirculation loop.

One drawback encountered in oligomerization processes during the use of reactors of this type is the management of the gas phase, also referred to as the gas headspace. Specifically, said gas headspace comprises gaseous compounds that are not very soluble in the liquid phase, and also ethylene that has not reacted in the process. The gas headspace is bled in order to eliminate said gaseous compounds. When the amount of ethylene present in the gas headspace is high, the bleeding of the gas headspace leads to a significant loss of unreacted ethylene, which is detrimental to the yield of the process and therefore to the cost of the oligomerization process.

In order to improve the efficiency of the oligomerization process, notably in terms of cost, it is therefore essential to limit the loss of unreacted ethylene contained in the gas headspace in order to improve the conversion thereof in said process.

Figure 1:
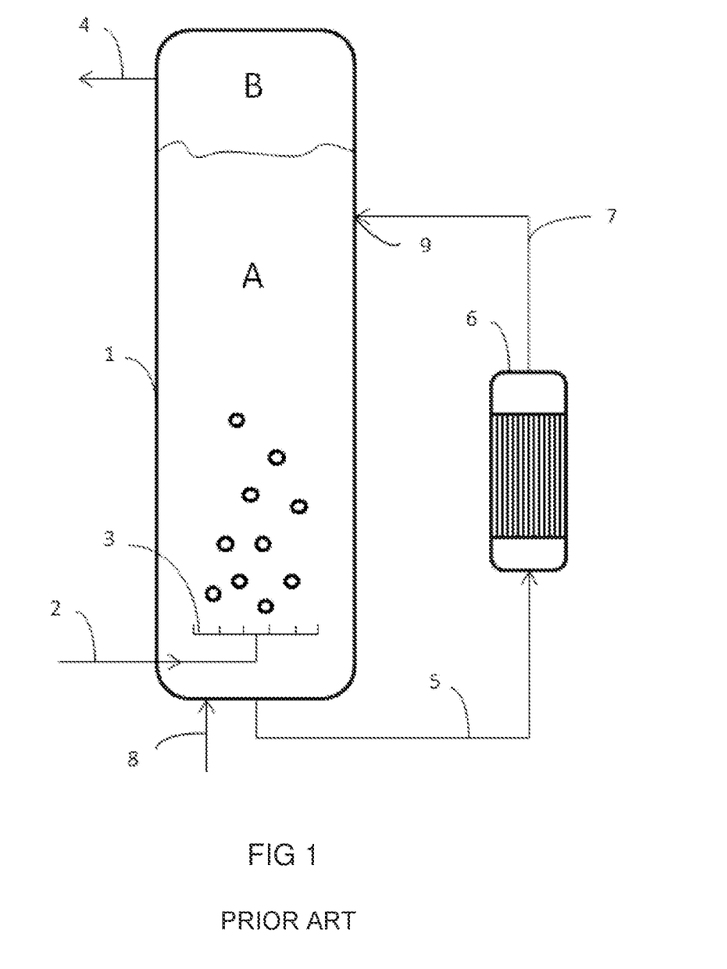

The processes of the prior art, employing a recirculation loop, as illustrated in FIG. 1, do not make it possible to limit the loss of ethylene and the bleeding of the gas headspace results in a departure of ethylene from the reactor which is detrimental to the yield of the process.

Application WO 2013/116922 discloses a process in which the gas headspace is directly introduced into the recirculation loop via a low-pressure system. This technology makes it possible to limit the accumulation of ethylene in the gas headspace but is accompanied by a loss of the homogeneity of the concentration of dissolved ethylene in the liquid phase within the reaction chamber.

Application WO 2009/060343 discloses the use of devices of Venturi or gas/liquid nozzle type in order to generate two-phase jets at the gas/liquid interphase, making it possible to dissolve the ethylene contained in the gas headspace. These types of devices consume energy, in particular in the form of a pressure drop in the recirculation loop, and also have the disadvantage of causing eddies at the gas/liquid interphase, which is unfavorable for the level control in the reactor.

Surprisingly, the applicant has discovered a process that uses a step of dispersing the ethylene contained in the gas headspace in the liquid fraction from the recirculation loop.

The oligomerization process according to the invention advantageously makes it possible to optimize the conversion of the ethylene involved in the process, and also to limit the cost of the implementation thereof. In particular, the process makes it possible to obtain linear olefins, and preferably alpha-olefins.

SUMMARY OF THE INVENTION

An object of the present invention is to provide an oligomerization process carried out at a pressure of between 0.1 and 10 MPa, at a temperature of between 30° C. and 200° C., comprising the following steps:
 a) a step of introducing the catalytic oligomerization system comprising a metal catalyst and an activating agent into a reaction chamber comprising a liquid phase and a gas phase,
 b) a step of bringing said catalytic system into contact with ethylene by introducing said ethylene into the lower part of the reaction chamber,
 c) a step of withdrawing a liquid fraction at a flow rate between 500 and 10 000 t/h in the lower part of the reaction chamber,
 d) a step of cooling the liquid fraction drawn off in step c) by passing said liquid fraction into a heat exchanger,
 e) a step of introducing the liquid fraction cooled in step d) at the top of the reaction chamber,
 f) a step of dispersing the liquid fraction introduced in step e) in the gas phase in the upper part of the reaction chamber,
wherein steps c) to e) constitute a recirculation loop.

One advantage of the present invention is to increase the contact surface area between the dispersed liquid fraction introduced at the top of the reaction chamber and the ethylene contained in the gas headspace, and thus to make it possible to increase the amount of ethylene dissolved in the dispersed liquid fraction. The ethylene thus dissolved is entrained in the liquid phase of the reaction chamber in order to bring it back into contact with the catalytic system. This step advantageously makes it possible to dissolve the unreacted ethylene contained in the gas headspace toward the liquid phase and thus to optimize its conversion in the oligomerization process.

Another advantage of the present invention is to improve the productivity of the device employed in the process.

BRIEF DESCRIPTION OF THE INVENTION

The present invention relates to an oligomerization process carried out at a pressure of between 0.1 and 10 MPa, at a temperature of between 30 and 200° C., comprising the following steps:
 a) a step of introducing the catalytic oligomerization system comprising a metal catalyst and an activating agent into a reaction chamber comprising a liquid phase and a gas phase,
 b) a step of bringing said catalytic system into contact with ethylene by introducing said ethylene into the lower part of the reaction chamber,
 c) a step of withdrawing a liquid fraction at a flow rate between 500 and 10 000 t/h in the lower part of the reaction chamber,
 d) a step of cooling the liquid fraction drawn off in step c) by passing said liquid fraction into a heat exchanger,
 e) a step of introducing the liquid fraction cooled in step d) at the top of the reaction chamber, f) a step of dispersing the liquid fraction introduced in step e) in the gas phase in the upper part of the reaction chamber, wherein steps c) to e) constitute a recirculation loop.

Preferably, the process is carried out in a device comprising a reaction chamber comprising a liquid phase and a gas phase, a loop for recirculating a liquid fraction toward a heat exchanger and a means capable of dispersing the liquid fraction within the gas phase of said reaction chamber.

Preferably, the catalytic systems introduced in step a) comprise at least one metal catalyst based on nickel, titanium or chromium, at least one activating agent, optionally in the presence of at least one additive and optionally in the presence of at least one solvent.

Preferably, the ethylene is introduced in step b) at a flow rate of between 1 and 250 t/h.

Preferably, a stream of hydrogen gas is introduced in step b) into the reaction chamber, with a flow rate representing 0.2 to 1% by weight of the flow rate of incoming ethylene.

Preferably, step d) makes it possible to reduce the temperature of the liquid fraction by 2° C. to 10° C.

Preferably, the cooled liquid fraction is introduced in step e) at a flow rate between 500 and 10 000 t/h.

Preferably, the surface area of exchange with the gas headspace of the liquid fraction in step f) is increased between 1.1 and 500 times with respect to the free surface area of the liquid volume introduced without dispersion.

Preferably, the dispersion step f) is carried out by a perforated dispersion means and preferably is selected from a perforated plate or a perforated distributor.

Preferably, the liquid fraction dispersed in step f) is dispersed in the form of droplets with a diameter of between 1 and 5 mm.

Preferably, liquid fraction dispersed in step f) is dispersed in the form of a thin film, preferably of less than 8 mm in thickness.

The present invention also relates to a gas/liquid oligomerization reaction device comprising:
- a reaction chamber i), of elongated shape along the vertical axis, comprising a liquid phase comprising and preferably consisting of the products of the reaction, dissolved ethylene, the catalytic system and an optional solvent, and a gas phase located above said liquid phase, comprising unreacted ethylene and also the non-condensable gases (notably methane), and
- a means for introducing ethylene ii), located in the lateral lower part of said reaction chamber, employing a means for distributing ethylene within said liquid phase of the reaction chamber,
- a means for introducing the catalytic system iii), comprising a metal catalyst, at least one activator and at least one additive, said means is located in the lower part of the reaction chamber,
- a recirculation loop iv) comprising a withdrawing means at the base (preferably at the bottom) of the reaction chamber for withdrawing a liquid fraction toward a heat exchanger enabling the cooling of said liquid, and a means for introducing said cooled liquid, said introduction being carried out in the gas phase at the top of the reaction chamber, characterized in that said introduction into the gas headspace v) is carried out via a means capable of dispersing the liquid cooled in the recirculation loop iv) in the gas headspace of the reaction chamber.

Preferably, the means for dispersing the cooled liquid fraction is selected from a distributor network, a perforated plate or a perforated distributor, having an open fraction of between 0.5% and 40%.

Preferably, the means for dispersing the cooled liquid fraction is selected from a packing having a large surface area with respect to the volume thereof and also a small pressure drop, preferably the ratio of the surface area with respect to the volume is between 40 and 2500 $m^2/m^3$.

Definitions & Abbreviations

Throughout the description, the terms or abbreviations below have the following meaning.

Oligomerization means any addition reaction of a first olefin with a second olefin identical to or different from the first olefin. The olefin thus obtained has the empirical formula $C_nH_{2n}$, where n is equal to or greater than 4.

α-Olefin is understood to mean an olefin in which the double bond is located at the terminal position of the alkyl chain.

Catalytic system is understood to mean the mixture of at least one metal catalyst and of at least one activating agent, in the presence optionally of at least one additive and optionally in the presence of at least one solvent.

Liquid phase is understood to mean the mixture of all of the compounds which are in a liquid physical state under the temperature and pressure conditions of the reaction chamber.

Gas phase or else gas headspace is understood to mean the mixture of all of the compounds which are in the gaseous physical state under the temperature and pressure conditions of the reaction chamber: in the form of bubbles present in the liquid, and also in the top part of the reactor (headspace of the reactor).

Lateral lower part of the reaction chamber is understood to mean a part of the shell of the reactor located in the bottom part and on the side.

Noncondensable gas is understood to mean an entity in gaseous physical form which only partially dissolves in the liquid at the temperature and pressure conditions of the reaction chamber and which can, under certain conditions, accumulate in the headspace of the reactor (example here: ethane).

t/h means the value of a flow rate expressed as tonne per hour.

Packing is understood to mean an element that makes it possible to disperse the liquid in the form of a thin film, which has a large surface area relative to its volume (from 50 to 2000 $m^2/m^3$) and also a small pressure drop.

Free surface area of the liquid volume is understood to mean the contact surface area of the cooled liquid fraction introduced into the gas headspace without dispersion means.

Dispersion of the liquid fraction is understood to mean the increase in the surface area of exchange between the gas phase and said liquid fraction.

The terms reactor or device denote all of the means which enable the implementation of the oligomerization process according to the invention, such as in particular the reaction chamber and the recirculation loop.

DETAILED DESCRIPTION OF THE INVENTION

It is specified that, throughout this description, the expression "of between . . . and . . . " should be understood as including the limits mentioned.

Within the meaning of the present invention, the various embodiments presented can be used alone or in combination with one another, without any limit to the combinations.

The present invention relates to an oligomerization process carried out at a pressure of between 0.1 and 10 MPa, at a temperature of between 30 and 200° C., comprising the following steps:
a) a step of introducing the catalytic oligomerization system comprising a metal catalyst and an activating agent into a reaction chamber comprising a liquid phase and a gas phase,
b) a step of bringing said catalytic system into contact with ethylene by introducing said ethylene into the lower part of the reaction chamber,
c) a step of withdrawing a liquid fraction at a flow rate of between 500 and 10 000 t/h in the lower part of the reaction chamber,
d) a step of cooling the liquid fraction withdrawn in step c) by passing said liquid fraction into a heat exchanger,
e) a step of introducing the liquid fraction cooled in step d) at the top of the reaction chamber,
f) a step of dispersing the liquid fraction introduced in step e) in the gas phase in the upper part of the reaction chamber,
wherein steps c) to e) constitute a recirculation loop.

Oligomerization Process

The oligomerization process according to the invention makes it possible to obtain linear olefins by bringing ethylene and a catalytic system into contact, optionally in the presence of a solvent.

In particular, the process relates to the oligomerization of ethylene to give linear olefins such as butene, hexene, octene, decene, preferably such as 1-butene, 1-hexene or 1-octene, alone or a mixture.

Any catalytic system known to a person skilled in the art and capable of being employed in the oligomerization process according to the invention comes within the field of the invention. Said catalytic systems and also the implementations thereof are described in particular in applications FR 2 984 311, FR 2 552 079, FR 3 019 064, FR 3 023 183, FR 3 042 989 or else in application FR 3 045 414. Preferably, the catalytic systems comprise at least one metal catalyst, preferably based on nickel, on titanium or on chromium, and at least one activating agent, optionally in the presence of at least one additive and optionally in the presence of at least one solvent.

Preferably, the nickel-based catalyst comprises a nickel catalyst with a (+II) oxidation state. Preferably, the nickel-based catalyst is chosen from nickel(II) carboxylates, such as, for example, nickel 2-ethylhexanoate, nickel(II) phenates, nickel(II) naphthenates, nickel(II) acetate, nickel(II) trifluoroacetate, nickel(II) triflate, nickel(II) acetylacetonate, nickel(II) hexafluoroacetylacetonate, $\eta^3$-allylnickel(II) chloride, $\pi$-allylnickel(II) bromide, methallylnickel(II) chloride dimer, $\eta^3$-allylnickel(II) hexafluorophosphate, $\eta^3$-methallylnickel(II) hexafluorophosphate and nickel(II) 1,5-cyclooctadienyl, in their hydrated or nonhydrated form, taken alone or as a mixture.

Preferably, the titanium-based catalyst comprises an alkoxy or aryloxy compound of titanium. Preferably, the titanium-based catalyst is chosen from titanium phenoxide, titanium 2-methylphenoxide, titanium 2,6-dimethylphenoxide, titanium 2,4,6-trimethylphenoxide, titanium 4-methylphenoxide, titanium 2-phenylphenoxide, titanium 2,6-diphenylphenoxide, titanium 2,4,6-triphenylphenoxide, titanium 4-phenylphenoxide, titanium 2-(tert-butyl)-6-phenylphenoxide, titanium 2,4-di(tert-butyl)-6-phenylphenoxide, titanium 2,6-diisopropylphenoxide, titanium 2,6-di(tert-butyl)phenoxide, titanium 4-methyl-2,6-di(tert-butyl)phenoxide, titanium 2,6-dichloro-4-(tert-butyl)phenoxide, titanium 2,6-dibromo-4-(tert-butyl)phenoxide, titanium biphenoxide, titanium binaphthoxide, titanium 1,8-naphthalenedioxide, titanium tetraethoxide, titanium tetraisopropoxide, titanium tetra(n-butoxide) or titanium tetra(2-ethylhexyloxide).

Preferably, the chromium compound can be a chromium (II) or chromium(III) salt but also a salt with a different oxidation state which can comprise one or more identical or different anions, such as, for example, halides, carboxylates, acetylacetonates or alkoxy or aryloxy anions. Preferably, the chromium-based catalyst is chosen from $CrCl_3$, $CrCl_3(tetrahydrofuran)_3$, $Cr(acetylacetonate)_3$, $Cr(naphthenate)_3$, $Cr(2-ethylhexanoate)_3$ or $Cr(acetate)_3$.

Preferably, an activating agent is at least one aluminum compound independently chosen from methylaluminum dichloride ($MeAlCl_2$), dichloroethylaluminum ($EtAlCl_2$), ethylaluminum sesquichloride ($Et_3Al_2Cl_3$), chlorodiethylaluminum ($Et_2AlCl$), chlorodiisobutylaluminum ($i-Bu_2AlCl$), triethylaluminum ($AlEt_3$), tripropylaluminum ($Al(n-Pr)_3$), triisobutylaluminum ($Al(i-Bu)_3$), diethylethoxyaluminum ($Et_2AlOEt$), methylaluminoxane (MAO), ethylaluminoxane and modified methylaluminoxanes (MMAO).

Preferably, an additive is at least one compound of ether type independently chosen from diethyl ether, diisopropyl ether, dibutyl ether, diphenyl ether, 2-methoxy-2-methylpropane, 2-methoxy-2-methylbutane, 2,2-dimethoxypropane, 2,2-di(2-ethylhexyloxy)propane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, di(2-methoxyethyl) ether, benzofuran, glyme and diglyme, taken alone or as a mixture.

Preferably, an additive is at least one compound of amine type independently chosen from trimethylamine, triethylamine, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, pyrrole, 2,5-dimethylpyrrole, N-methylpyrrole, N-butylpyrrole, N-methylimidazole, N-butylimidazole, 2,2'-bipyridine, N,N'-dimethylethane-1, 2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine.

Preferably, an additive is at least one compound of phosphine type independently chosen from tributylphosphine, triisopropylphosphine, tricyclopentylphosphine, tricyclohexylphosphine, triphenylphosphine, tris(o-tolyl)phosphine, bis(diphenylphosphino)ethane, trioctylphosphine oxide, triphenylphosphine oxide or triphenyl phosphite.

Preferably, an additive is at least one aryloxy compound of an element M chosen from the group formed by magnesium, calcium, strontium and barium, preferably magnesium, of general formula $[M(RO)_{2-n}X_n]_y$, in which RO is an aryloxy group of an ROH derivative containing from 6 to 80 carbon atoms, X is a halogen or a hydrocarbyl radical containing from 1 to 30 carbon atoms, n is an integer which can take the values of 0 or 1, and y is an integer of between 1 and 10, preferably y is equal to 1 or 2 or 3 or 4. Mention may be made, among the preferred aryloxy radicals, as non-limiting examples, of: 4-phenylphenoxy, 2-phenylphenoxy, 2,6-diphenylphenoxy, 2,4,6-triphenylphenoxy, 2,3,5,6-tetraphenylphenoxy, 2-(tert-butyl)-6-phenylphenoxy, 2,4-di(tert-butyl)-6-phenylphenoxy, 2,6-diisopropylphenoxy, 2,6-dimethylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy. The two aryloxy radicals can be borne by one and the same molecule, such as, for example, the biphenoxy radical, binaphthoxy or 1,8-naphthalenedioxy, which are optionally substituted by alkyl, aryl or halide radicals. Preferably, the aryloxy radical RO is 2,6-diphenylphenoxy, 2-(tert-butyl)-6-phenylphenoxy or 2,4-di(tert-butyl)-6-phenylphenoxy.

Preferably, an additive is at least one compound corresponding to the general formula (I) or one of the tautomers of said compound.

(I)

in which:
A and A', which are identical or different, are independently an oxygen or a single bond between the phosphorus atom and a carbon atom,
the $R^{1a}$ and $R^{1b}$ groups are independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 2-methylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-di(trifluoromethyl)phenyl, benzyl, naphthyl, bisnaphthyl, pyridyl, bisphenyl, furanyl or thiophenyl groups,
the $R^2$ group is independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-bis(trifluoromethyl)phenyl, benzyl, naphthyl, bisnaphthyl, pyridyl, bisphenyl, furanyl or thiophenyl groups.

Preferably, the linear olefins obtained comprise from 4 to 20 carbon atoms, preferably from 4 to 18 carbon atoms, preferably from 4 to 10 carbon atoms and preferably from 4 to 8 carbon atoms. Preferably, the olefins are linear α-olefins chosen from but-1-ene, hex-1-ene or oct-1-ene.

In one embodiment, a solvent or a mixture of solvents can be used in the oligomerization process. Said solvent is independently chosen from the group formed by aliphatic and cycloaliphatic hydrocarbons, such as hexane, cyclohexane, heptane, butane or isobutane.

The oligomerization process is carried out at a pressure of between 0.1 and 10 MPa and preferably between 0.3 and 8 MPa, at a temperature of between 30 and 200° C. and preferentially between 35 and 150° C., and the flow rate of the liquid recirculation loop is of between 500 and 10 000 t/h and preferably between 800 and 7000 t/h.

Preferably, the concentration of catalyst in the catalytic system is of between 0.1 and 50 ppm by weight of atomic metal, with respect to the reaction mass, preferably between 0.5 and 20 ppm and preferably between 0.8 and 10 ppm.

According to one embodiment, the oligomerization process is carried out batchwise. The catalytic system, constituted as described above, is introduced into a reactor provided with the usual stirring, heating and cooling devices, then pressurization with ethylene is carried out to the desired pressure, and the temperature is adjusted to the desired value. The oligomerization device is maintained at a constant pressure by introduction of ethylene until the total volume of liquid produced represents, for example, from 2 to 50 times the volume of the catalytic solution introduced beforehand. The catalyst is then destroyed by any usual means known to a person skilled in the art and then the products of the reaction and the solvent are withdrawn and separated.

According to another embodiment, the oligomerization process is carried out continuously. The catalytic system, constituted as described above, is injected at the same time as the ethylene into a reactor stirred by conventional mechanical means known to a person skilled in the art or by external recirculation, and maintained at the desired temperature. The components of the catalytic system can also be injected separately into the reaction medium. The ethylene is introduced by an intake valve under the control of the pressure, which keeps the latter constant in the reactor. The reaction mixture is withdrawn by means of a valve under the control of the liquid level, so as to keep the latter constant. The catalyst is destroyed continuously by any usual means known to a person skilled in the art and then the products resulting from the reaction, and also the solvent, are separated, for example by distillation. The ethylene which has not been converted can be recycled in the reactor. The catalyst residues included in a heavy fraction can be incinerated.

Step a) of Introducing the Catalytic System

The process according to the invention comprises a step a) of introducing the catalytic system comprising a metal catalyst and an activating agent, and optionally of introducing a solvent or a mixture of solvents, into a reaction chamber comprising a liquid phase and a gas phase.

Preferably, the catalytic system is introduced in the lower part of the reaction chamber and preferably in the bottom of the reaction chamber.

Preferably, the pressure for introduction into the reaction chamber is between 0.1 and 10 MPa, preferably between 0.3 and 8 MPa.

Preferably, the temperature for introduction into the reaction chamber is between 30° C. and 200° C., preferably between 35° C. and 150° C.

Step b) of Bringing into Contact with Ethylene

The process according to the invention comprises a step b) of bringing the catalytic system introduced in step a) into contact with ethylene. Said ethylene is introduced at the lower part of the reaction chamber, preferably on the lateral lower part of the reaction chamber.

Preferably, the ethylene is distributed by dispersion during its introduction into the lower liquid phase of the reaction chamber by a means capable of producing said dispersion uniformly over the entire cross section of the reactor. Preferably, the dispersion means is chosen from a distributor network with a homogeneous distribution of the ethylene injection points over the entire cross section of the reactor.

Preferably, the gaseous ethylene is introduced at a flow rate of between 1 and 250 t/h, preferably between 3 and 200 t/h, preferably between 5 and 150 t/h and preferably between 10 and 100 t/h.

According to a specific embodiment of the invention, a stream of gaseous hydrogen can also be introduced into the reaction chamber, with a flow rate representing from 0.2% to 1% by weight of the flow rate of incoming ethylene. Preferably, the stream of gaseous hydrogen is introduced by the pipe employed for the introduction of the gaseous ethylene.

Step c) of Withdrawing a Fraction of the Liquid Phase

The process according to the invention comprises a step c) of withdrawing a fraction of the liquid phase in the lower part of the reaction chamber.

The withdrawal carried out in step c) is performed in the lower part of the reaction chamber, preferably below the level of the ethylene injection and preferably in the bottom of the chamber. The withdrawal is carried out by any means capable of carrying out the withdrawal and preferably by a pump.

Preferably, the withdrawal flow rate is between 500 and 10 000 t/h and preferably between 800 and 7000 t/h.

According to a preferred embodiment, the liquid fraction withdrawn from the liquid phase is divided into two streams. The first "main" stream is sent to the cooling step d). The second stream corresponds to the effluent obtained on conclusion of the oligomerization process and can be sent to a separation section located downstream of the device employed in the process according to the invention. Advantageously, the flow rate of said effluent is regulated in order to maintain a constant liquid level in the reactor. Preferably, the flow rate of said effluent is from 5 to 200 times lower than the liquid flow rate sent to the cooling step. Preferably, the flow rate of said effluent is from 5 to 150 times lower, preferably from 10 to 120 times lower and preferably from 20 to 100 times lower.

Step d) of Cooling the Liquid Fraction

The process according to the invention comprises a step d) of cooling the liquid fraction withdrawn in step c).

Preferably, the cooling step is carried out by the circulation of the main liquid stream withdrawn in step c) through one or more heat exchangers located inside or outside the reaction chamber and preferably outside.

The heat exchanger makes it possible to reduce the temperature of the liquid fraction by 2 to 10° C., preferably by 3 to 9° C., preferably by 4 to 8° C. Advantageously, the cooling of the liquid fraction makes it possible to keep the temperature of the reaction medium within the desired temperature ranges.

Advantageously, carrying out the step of cooling the liquid via the recirculation loop also makes it possible to carry out the stirring of the reaction medium and thus to homogenize the concentrations of the reactive entities throughout the liquid volume of the reaction chamber.

Step e) of Introducing the Cooled Liquid Fraction

The process according to the invention comprises a step e) of introducing the liquid fraction cooled in step d).

The introduction of the cooled liquid fraction resulting from step d) is carried out in the gaseous portion of the reaction chamber, preferably at the top of said chamber, by any means known to a person skilled in the art.

Preferably, the flow rate for introduction of the cooled liquid fraction is between 500 and 10 000 t/h and preferably between 800 and 7000 t/h.

Step f) of Dispersing the Liquid Fraction Introduced in Step e)

In the absence of any particular device, the available surface area for the gas-liquid exchanges in the headspace of the reactor is the free surface area of the liquid volume.

The process according to the invention comprises a step f) of dispersing the liquid fraction introduced in step e) in the gas headspace of the reaction chamber.

Advantageously, said step of dispersing the cooled liquid fraction during the introduction thereof into the gas headspace of the reaction chamber increases the contact surface area, also referred to as the surface area of exchange, between the dispersed liquid and the gaseous ethylene contained in the gas headspace and thus makes it possible to facilitate the dissolving of the ethylene in the dispersed liquid. The ethylene thus dissolved is entrained in the liquid phase of the reaction chamber in order to bring it back into contact with the catalytic system. This step makes it possible to recycle the unreacted ethylene contained in the gas headspace toward the liquid phase and thus to optimize its conversion in the oligomerization process according to the invention, and thus to improve the productivity of the reactor.

The dispersing step is carried out by a means capable of dispersing the liquid fraction in the gas headspace of the reaction chamber. According to a particular arrangement, the dispersion means is perforated and preferably is chosen from a perforated plate or a perforated distributor.

According to another particular arrangement, the dispersion means is unperforated and is chosen from a packing in order to increase the gas-liquid exchange surface area in the gas headspace, this solution being reserved for the reactions that do not give rise to fouling problems. Packing is understood to mean an element that makes it possible to disperse the liquid in the form of a thin film, which has a large surface area relative to its volume, preferably the ratio of the surface area relative to the volume is between 40 and 2500 $m^2/m^3$, preferably between 50 and 2000 $m^2/m^3$, and preferably between 80 and 1500 $m^2/m^3$.

According to a preferred embodiment, the liquid fraction can be dispersed in the form of droplets with a diameter of between 0.2 and 10 millimeters (mm), preferably between 0.3 and 8 mm, preferably between 0.5 and 6 mm, and preferably between 1 and 5 mm.

According to another preferred embodiment, the liquid fraction can be dispersed in the form of a thin film, preferably of less than 8 mm, preferably of less than 5 mm, preferably of between 1 and 5 mm, and preferably of between 1 and 4 mm in thickness.

According to another preferred embodiment, the liquid fraction can be dispersed by at least one perforated dispersion means in combination with at least one unperforated dispersion means.

Preferably, the surface area of exchange with the gas headspace is increased between 1.1 and 500 times, and preferably between 1.5 and 200 times with respect to the free surface area of the liquid volume introduced without dispersion.

Oligomerization Reaction Device

Numerous reactors employing a gas/liquid mixture are formed of a reaction chamber comprising a liquid phase and a gas phase, a loop for recirculation of a liquid fraction toward a heat exchanger making possible the cooling of the liquid fraction before it is reinjected into the main chamber.

Commonly, the high flow rate circulating in the recirculation loop makes it possible to obtain good homogenization of the concentrations and to control the temperature in the liquid fraction within the reaction chamber.

Another subject according to the present invention relates to the device capable of implementing the process according to the invention.

The reaction device employed by the process according to the invention belongs to the field of gas/liquid reactors commonly referred to as bubble point reactors. In particular, the reaction device according to the invention comprises the following elements:

- a reaction chamber i), of elongated shape along the vertical axis, comprising a liquid phase comprising and preferably consisting of the products of the reaction, dissolved ethylene, the catalytic system and an optional solvent, and a gas phase located above said liquid phase comprising unreacted ethylene and also the noncondensable gases (in particular methane), and
- a means for introducing ethylene ii), located in the lateral lower part of said reaction chamber, employing a means for distributing ethylene within said liquid phase of the reaction chamber,
- a means for introducing the catalytic system iii), comprising a metal catalyst, at least one activator and at least one additive, said means being located in the lower part of the reaction chamber,
- a recirculation loop iv) comprising a withdrawing means at the base (preferably at the bottom) of the reaction chamber for withdrawing a liquid fraction toward a heat exchanger enabling the cooling of said liquid, and a means for introducing said cooled liquid, said introduction being carried out in the gas phase at the top of the reaction chamber, characterized in that said introduction into the gas headspace v) is carried out via a means capable of dispersing said cooled liquid in the gas headspace of the reaction chamber.

i) A Reaction Chamber

According to the invention, any reaction chamber known to a person skilled in the art and capable of carrying out the process according to the invention can be envisaged. Preferably, the reaction chamber is of cylindrical shape and has a height to width ratio (denoted H/D) of between 1 and 8, preferably between 1 and 4.

Preferably, the reaction chamber comprises a means for bleeding off the non-condensable gases.

Preferably, the reaction chamber also comprises a pressure sensor which makes it possible to keep the pressure within the reaction chamber constant. Preferably, said pressure is kept constant by introducing additional ethylene into the reaction chamber.

Preferably, the reaction chamber also comprises a liquid level sensor; said level is kept constant by adjusting the flow rate of the effluent withdrawn in step c). Preferably, the level sensor is located at the interphase between the liquid phase and the gas headspace.

ii) A Means for Introducing Ethylene

According to the invention, the reaction chamber i) comprises a means for introducing gaseous ethylene located in the lower part of said chamber, more particularly in the lateral lower part.

Preferably, the means ii) for introducing ethylene is chosen from a pipe, a network of pipes, a multitubular distributor, a perforated plate or any other means known to a person skilled in the art.

In a particular embodiment, the means for introducing ethylene is located in the recirculation loop iv).

Preferably, a gas distributor, which is a device which makes it possible to disperse the gas phase uniformly over the entire liquid section, is positioned at the end of the introduction means ii) within the reaction chamber i). Said device comprises a network of perforated pipes, the diameter of the orifices of which is between 1 and 12 mm, preferably between 3 and 10 mm, in order to form ethylene bubbles in the liquid of millimetric size.

Preferably, the velocity of the ethylene at the outlet of the orifices is between 1 and 30 m/s. Its superficial velocity (volume velocity of gas divided by the cross section of the reaction chamber) is between 0.5 and 10 cm/s and preferably between 1 and 8 cm/s.

iii) A Means for Introducing the Catalytic System

According to the invention, the reaction chamber i) comprises a means iii) for introducing the catalytic system.

Preferably, the introduction means iii) is located on the lower part of the reaction chamber and preferably at the bottom of said chamber.

According to an alternative embodiment, the catalytic system is introduced into the recirculation loop.

The means iii) for introducing the catalytic system is chosen from any means known to a person skilled in the art and is preferably a pipe.

In the embodiment in which the catalytic system is employed in the presence of a solvent or of a mixture of solvents, said solvent is introduced by an introduction means located in the lower part of the reaction chamber, preferably at the bottom of the reaction chamber or else in the recirculation loop.

iv) A Recirculation Loop

According to the invention, the liquid phase is rendered homogeneous and also the temperature is regulated within the reaction chamber by the use of a recirculation loop comprising a means on the lower part of the reaction chamber, preferably at the bottom, in order to withdraw a liquid fraction toward one or more heat exchanger(s) enabling the cooling of said liquid, and a means for introducing said cooled liquid into the gas headspace at the top of the reaction chamber.

The recirculation loop can advantageously be implemented by any necessary means known to a person skilled in the art, such as a pump for the withdrawal of the liquid fraction, a means capable of regulating the flow rate of the liquid fraction withdrawn, or else a pipe for bleeding off at least one portion of the liquid fraction.

Preferably, the means for withdrawing the liquid fraction from the reaction chamber is a pipe.

The heat exchanger(s) capable of cooling the liquid fraction is (are) chosen from any means known to a person skilled in the art.

The recirculation loop enables good homogenization of the concentrations and makes it possible to control the temperature in the liquid fraction within the reaction chamber.

v) Means for Dispersing the Cooled Liquid Fraction

According to the invention, the liquid fraction cooled in the recirculation loop iv) is introduced into a dispersion means located at the top of the reaction chamber level with the gas headspace. Said means makes it possible, according to the invention, to disperse the liquid within the gas headspace. Preferably, the exchange surface area with the gas headspace is thus increased between 1.1 and 500 times with respect to the free surface area of the liquid volume introduced without dispersion means, preferably between 1.5 and 300 times, preferably between 2.0 and 200 times, preferably between 2.5 and 150 times, preferably between 3.0 and 100 times and more preferably still between 3.5 and 50 times.

Dispersion is understood to mean the fact of converting the liquid flow into a multitude of droplets or liquid streams, thus enabling the consequent increase in the contact surface area between the liquid and gas phases.

Preferably, the means for dispersing the cooled liquid fraction is chosen from a distributor network, a perforated plate or a perforated distributor, having a perforated surface area of between 0.5% and 40%, preferably between 1.0% and 30%, of preferably between 1.2% and 25%, preferably between 1.4% and 20% and preferably 1.6% and 15%.

Preferably, the dispersion means is unperforated and is chosen from a packing in order to increase the gas-liquid exchange surface area in the gas headspace, this solution being reserved for the reactions that do not give rise to fouling problems. Packing is understood to mean an element that makes it possible to disperse the liquid in the form of a thin film, which has a large surface area relative to its volume, and also a low pressure drop, preferably the ratio of the surface area relative to the volume is between 30 and 2000 $m^2/m^3$, preferably between 50 and 1500 $m^2/m^3$, preferably between 70 and 1200 $m^2/m^3$, preferably between 80 and 1000 $m^2/m^3$ and preferably between 100 and 800 $m^2/m^3$.

The dispersion means v) advantageously makes it possible to dissolve the unreacted ethylene contained in the gas headspace in order to reintroduce it into the liquid phase of the reaction chamber.

Specifically, the ethylene introduced at the base of the reaction chamber is dissolved in the liquid phase in which it undergoes the oligomerization reaction in contact with the catalytic system. The unreacted ethylene passes through the liquid phase until it reaches the gas headspace in which it accumulates. The reintroduction of the unreacted ethylene present in the gas headspace, into the liquid phase and therefore in contact with the catalytic system, thus makes it possible to improve the productivity of the reactor.

The dispersing step is carried out by a means capable of dispersing the liquid fraction in the gas headspace of the reaction chamber. Preferably, the dispersion means is perforated and is chosen from a perforated plate or a perforated distributor and preferably is located directly level with the means for introducing the liquid fraction cooled in the recirculation loop. The dimensions of the perforated surface area cover from 5% to 100%, preferably from 10% to 85%, preferably from 15% to 75% of the total cross section of the reactor on a perforated surface area of 15% to 50% of the cross section of the reactor. Preferably the dimensions of the perforations are between 0.5 and 10 mm, preferably between 0.8 and 8 mm, and preferably between 1 and 5 mm.

One advantage of the present invention is therefore to enable the unreacted ethylene to be brought back into contact with the reaction medium and thus to optimize the conversion of said ethylene to give linear olefins and preferably linear alpha-olefins.

BRIEF DESCRIPTION OF THE DRAWINGS

FIG. 1 illustrates a reaction device according to the prior art. This device consists of a reaction chamber (1) comprising a liquid phase A and a gas phase B also referred to as gas headspace, a means for introducing gaseous ethylene (2) in a gas distributor (3) into the liquid phase A. The gas headspace B comprises a bleed means (4). In the bottom of the reaction chamber (1) is a pipe for withdrawing a liquid fraction (5), toward a heat exchanger (6), the liquid fraction thus cooled is sent via a pipe (7) to the liquid phase A via an introduction means (9). The pipe (8) in the bottom of the reaction chamber allows the introduction of the catalytic system.

FIG. 2 illustrates a device enabling the implementation of the process according to the invention. Said device differs from the device of FIG. 1 in that the cooled liquid fraction is introduced via an introduction means (9) into the gas headspace B of the reaction chamber (1). The fraction thus introduced is then dispersed in the form of droplets by means of a perforated dispersion plate (10).

FIGS. 2 and 3 schematically illustrate particular embodiments of the subject of the present invention.

EXAMPLES

The examples below illustrate the invention without limiting the scope thereof.

The oligomerization process in the following examples is carried out at a pressure of 2.6 MPa, at a temperature of 45° C. The catalytic system introduced into the reaction chamber comprises, as nickel catalyst, Ni (2-ethylhexanoate)$_2$ at a concentration of 3 ppm by weight of nickel, tricyclohexylphosphine at a molar ratio of 10 molar equivalents of tricyclohexylphosphine to the nickel catalyst, and 15 molar equivalents of ethylaluminum dichloride relative to the nickel catalyst in the presence of n-heptane as solvent.

The oligomerization process in the examples below is carried out in a device, the internal diameter of the reaction chamber of which is 2.6 m. The height of the liquid phase is 5.1 m, and the total volume of the reaction chamber is 37 $m^3$. The height of the gas headspace is 2 m. The volume of the recirculation loop is 3 $m^3$.

The reaction kinetics can be expressed as the product of an apparent constant K and the concentration of dissolved ethylene in the liquid denoted [$C_2$]. The constant K is equal to $1.26 \times 10^{-3}$ $s^{-1}$.

Example 1: Comparative Example Corresponding to FIG. 1

The ethylene oligomerization process is carried out in a bubble point device, in which the introduction of the cooled liquid fraction originating from the recirculation loop is carried out in the liquid phase of the reaction chamber, below the level of the gas-liquid interface.

The flow rate of the recirculation loop is 625 t/h.

In this implementation, the surface area of exchange between the gas and liquid phases is limited to the free surface area of the liquid and corresponds to 5.3 $m^2$.

The overall residence time in the reactor is 164.5 min.

The volumetric productivity of this reactor is 152 kg of oligomer produced per hour and per $m^3$ of reactor.

Example 2: According to the Invention Corresponding to FIG. 2

Figure 2:
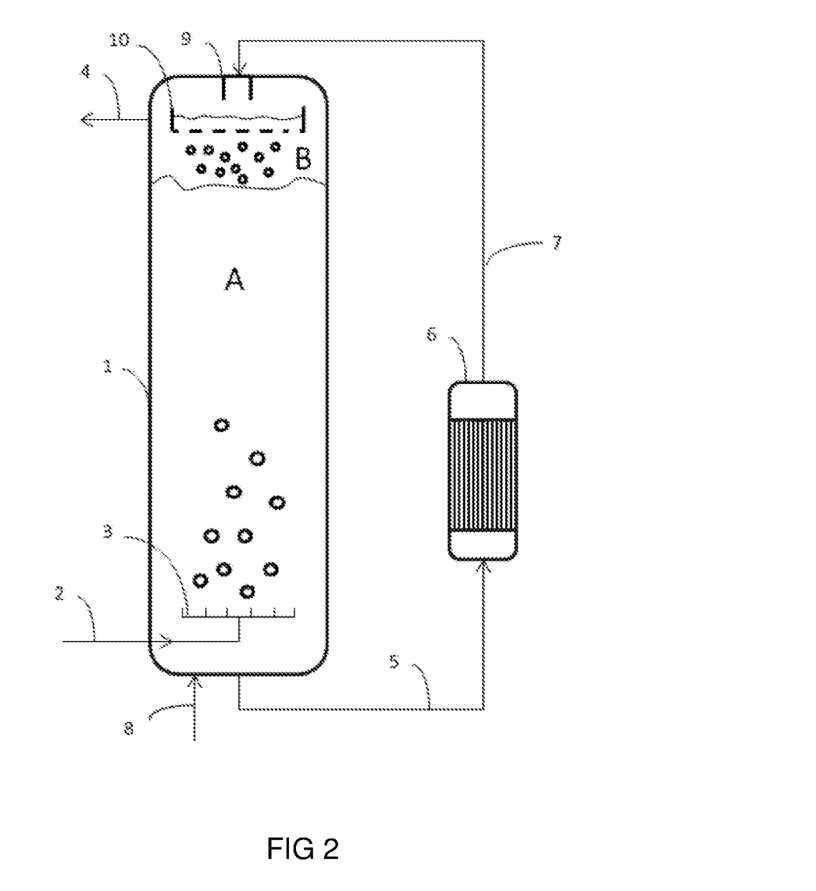
Figure 3:
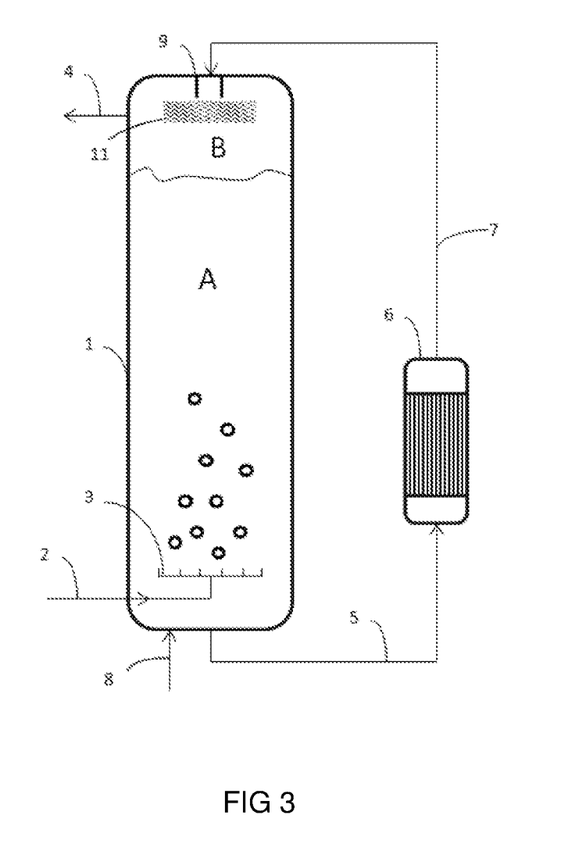
FIG. 3 illustrates a second device enabling the implementation of the process according to the invention. Said device differs from that used in FIG. 2 in that the cooled liquid fraction introduced via the means (9) is dispersed in the form of a film by means of a packing element.

The oligomerization process according to the invention is carried out in a device having dimensions identical to the one used in example 1, further comprising and in accordance with the invention a means capable of dispersing the cooled liquid fraction originating from the recirculation loop in the gas headspace of the reaction chamber. The flow rate of the recirculation loop is 1640 t/h. Said dispersion means is a perforated plate with a diameter of 2.3 m, composed of a plate perforated with holes of 1 mm, with a perforated surface area of 30%. The plate is equipped with edges that are 35 cm high.

In this case, the gas-liquid exchange surface area is multiplied by 110, which makes it possible to proportionally improve the transfer of material between the gas and liquid phases compared to the case of the conventional reactor without a dispersion element.

The overall residence time in the reactor is 54.4 min.

The volumetric productivity of this reactor is thus 399 kg of oligomer produced per hour and per $m^3$ of reactor, which is 2.6 times greater than that of the previous case, which clearly illustrates the gain in productivity achieved by the oligomerization process according to the invention by means of the dispersion of the cooled liquid fraction in the gas headspace of the reaction chamber.

The invention claimed is:

1. A gas/liquid oligomerization reaction device, comprising:
    a reaction chamber i), of elongated shape along the vertical axis, comprising a liquid phase comprising products of the reaction, dissolved ethylene, a catalytic system and an optional solvent, and a gas phase located above said liquid phase, comprising unreacted ethylene and also non-condensable gases, and
    a an ethylene introducer ii), located in the lateral lower part of said reaction chamber, employing an ethylene distributor within said liquid phase of the reaction chamber,
    a catalytic system introducer iii), said catalytic system comprising a metal catalyst, and at least one activating agent, said catalytic system introducer located in the lower part of the reaction chamber,
    a recirculation loop iv) comprising a device at the base of the reaction chamber withdrawing a liquid fraction toward a heat exchanger enabling the cooling of said liquid, and an introducer of resulting cooled liquid, introduction being carried out in gas phase at the top of the reaction chamber,
    wherein
    said introduction into gas headspace v) is carried out via a disperser of the liquid cooled in the recirculation loop iv) in the gas headspace of the reaction chamber.

2. The device as claimed in claim 1, wherein the disperser of the cooled liquid fraction is a distributor network, a perforated plate or a perforated distributor, having an open fraction of between 0.5% and 40%.

3. The device as claimed in claim 1, wherein the disperser of the cooled liquid fraction is a packing having a large surface area with respect to the volume thereof and also a small pressure drop.

4. An oligomerization process employing a device as claimed in claim 1, said process is carried out at a pressure between 0.1 and 10 MPa, at a temperature between 30° C. and 200° C., comprising:

a) introducing the catalytic system comprising the metal catalyst and activating agent into the reaction chamber i), said catalytic system comprising a liquid phase and a gas phase,
    b) bringing said catalytic system into contact with ethylene by introducing said ethylene into the lower part of the reaction chamber i),
    c) withdrawing a liquid fraction,
    d) cooling the liquid fraction drawn off in c) by passing said liquid fraction into a heat exchanger,
    e) introducing the liquid fraction cooled in d) at the top of the reaction chamber i),
    f) dispersing the liquid fraction introduced in e) in the gas phase in the upper part of the reaction chamber i),
    wherein c) to e) constitute a recirculation loop.

5. The process as claimed in claim 4, wherein the device comprises a reaction chamber comprising a liquid phase and a gas phase, a loop for recirculating a liquid fraction toward a heat exchanger and a disperser dispersing the liquid fraction within the gas phase of said reaction chamber.

6. The process as claimed in claim 4, wherein the catalytic system introduced in a) comprises at least one metal catalyst based on nickel, titanium or chromium, at least one activating agent, optionally in the presence of at least one additive and optionally in the presence of at least one solvent.

7. The process as claimed in claim 4, wherein the ethylene is introduced in b) at a flow rate between 1 and 250 t/h.

8. The process as claimed in claim 4, wherein a stream of hydrogen gas is introduced in b) into the reaction chamber, with a flow rate representing 0.2 to 1% by weight of the flow rate of incoming ethylene.

9. The process as claimed in claim 4, wherein d) makes it possible to reduce the temperature of the liquid fraction by 2° C. to 10° C.

10. The process as claimed in claim 4, wherein the cooled liquid fraction is introduced in e) at a flow rate between 500 and 10 000 t/h.

11. The process as claimed in claim 4, wherein the surface area of exchange with the gas headspace of the liquid fraction introduced in f) is increased between 1.1 and 500 times with respect to the free surface area of the liquid volume introduced without dispersion.

12. The process as claimed in claim 4, wherein the dispersion f) is carried out by a perforated dispersion means.

13. The process as claimed in claim 4, wherein the liquid fraction dispersed in f) is dispersed in the form of droplets with a diameter of between 1 and 5 mm.

14. The process as claimed in claim 4, wherein the liquid fraction dispersed in f) is dispersed in the form of a thin film.

15. The process as claimed in claim 12, wherein the perforated dispersion means is a perforated plate or a perforated distributor.

16. The device as claimed in claim 3, wherein the ratio of the surface area with respect to the volume is between 40 and 2500 $m^2/m^3$.

17. The process as claimed in claim 14, wherein the thin film is less than 8 mm in thickness.

18. The process as claimed in claim 1, wherein the liquid phase consists of products of the reaction, dissolved ethylene, a catalytic system and an optional solvent.

* * * * *